US011471139B2

(12) United States Patent
Inoue

(10) Patent No.: US 11,471,139 B2
(45) Date of Patent: Oct. 18, 2022

(54) MEDICAL MANIPULATOR AND MANIPULATION METHOD OF MEDICAL MANIPULATOR

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1003 days.

(21) Appl. No.: 16/196,352

(22) Filed: Nov. 20, 2018

(65) Prior Publication Data
US 2019/0083078 A1 Mar. 21, 2019

Related U.S. Application Data

(63) Continuation of application No. PCT/JP2016/065754, filed on May 27, 2016.

(51) Int. Cl.
*A61B 34/00* (2016.01)
*A61B 17/00* (2006.01)
(Continued)

(52) U.S. Cl.
CPC ........ *A61B 17/00234* (2013.01); *A61B 1/008* (2013.01); *A61B 1/0056* (2013.01); *A61B 1/01* (2013.01); *A61B 1/313* (2013.01); *A61B 5/065* (2013.01); *A61B 34/70* (2016.02); *A61B 34/71* (2016.02); *B25J 9/06* (2013.01); *B25J 9/1005* (2013.01); *B25J 9/106* (2013.01); *B25J 18/06* (2013.01); *A61B 34/74* (2016.02); *A61B 2017/00017* (2013.01);
(Continued)

(58) Field of Classification Search
CPC ....... A61B 85/065; A61B 34/71; A61B 34/74; B25J 9/06; B25J 9/1005; B25J 9/106
See application file for complete search history.

(56) References Cited

U.S. PATENT DOCUMENTS

2009/0143642 A1 6/2009 Takahashi et al.
2010/0236352 A1* 9/2010 Iida .................. B25J 18/06
73/862.391
(Continued)

FOREIGN PATENT DOCUMENTS

CN 101115432 A 1/2008
JP H06-047052 A 2/1994
(Continued)

OTHER PUBLICATIONS

International Search Report dated Aug. 16, 2016 issued in PCT/JP2016/065754.
Chinese Office Action dated Aug. 4, 2020 in Chinese Patent Application No. 201680085996.8.

*Primary Examiner* — Dale Moyer
(74) *Attorney, Agent, or Firm* — Scully, Scott, Murphy & Presser, P.C.

(57) ABSTRACT

A medical manipulator includes: an insertion portion, an end effector, a bend restraining unit, a position detector, an operation unit, a first drive unit, and a control unit. The control unit is configured to generate the first drive signal based on an output and the position of the bend restraining unit which is detected by the position detector. The output is output from the operation unit that operates the bending portion.

14 Claims, 10 Drawing Sheets

(51) Int. Cl.
  *A61B 1/313* (2006.01)
  *B25J 9/06* (2006.01)
  *B25J 9/10* (2006.01)
  *B25J 18/06* (2006.01)
  *A61B 1/005* (2006.01)
  *A61B 1/008* (2006.01)
  *A61B 1/01* (2006.01)
  *A61B 5/06* (2006.01)
  *A61M 25/01* (2006.01)

(52) U.S. Cl.
  CPC ............... *A61B 2017/00314* (2013.01); *A61B 2017/00327* (2013.01); *A61B 2017/00398* (2013.01); *A61M 25/0113* (2013.01); *A61M 25/0138* (2013.01); *A61M 25/0147* (2013.01)

(56) References Cited

U.S. PATENT DOCUMENTS

2014/0309625 A1\* 10/2014 Okamoto ............... A61B 34/71
  606/1
2016/0135913 A1   5/2016 Kishi et al.

FOREIGN PATENT DOCUMENTS

| JP | H09-168506 A | 6/1997 |
| JP | 2005-074148 A | 3/2005 |
| JP | 2009-131374 A | 6/2009 |
| JP | 2010-178886 A | 8/2010 |
| JP | 2014-028007 A | 2/2014 |
| JP | 2015-023951 A | 2/2015 |
| WO | WO 2015/125797 A1 | 8/2015 |

\* cited by examiner

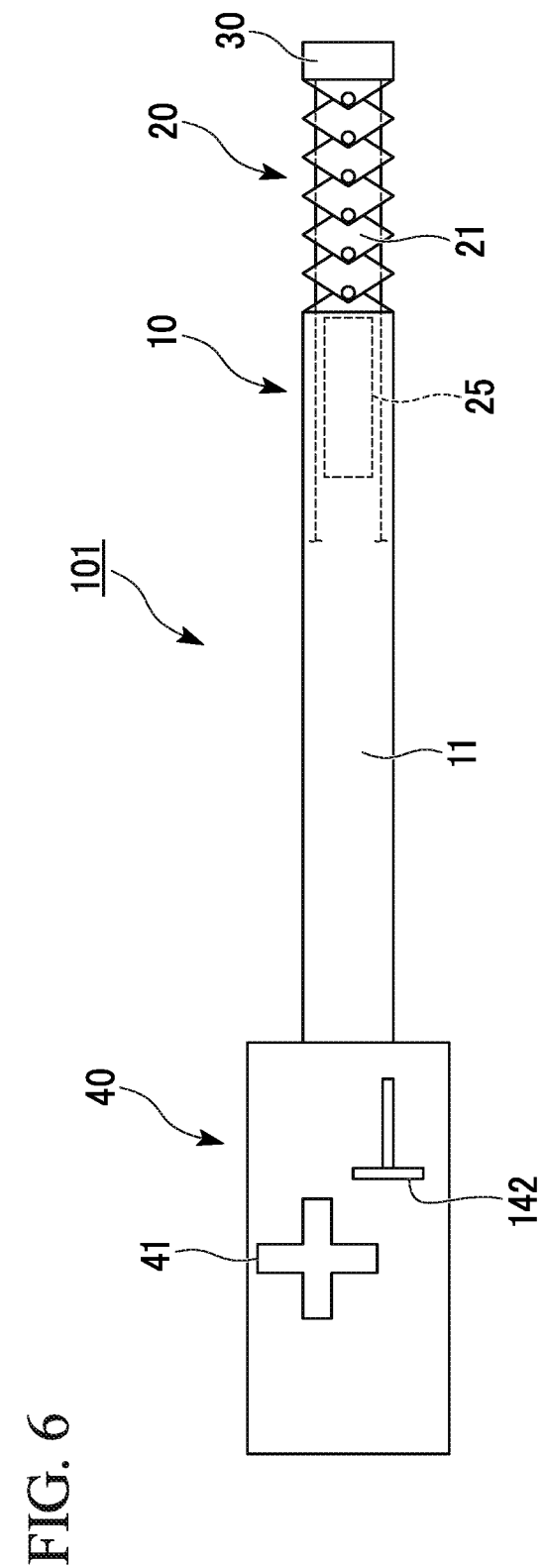

MEDICAL MANIPULATOR AND MANIPULATION METHOD OF MEDICAL MANIPULATOR

This application is a continuation application based on a PCT Patent Application No. PCT/JP2016/065754, filed on May 27, 2016. The content of the PCT Application is incorporated herein by reference.

BACKGROUND OF THE INVENTION

Field of the Invention

The present invention relates to a medical manipulator and a manipulation method of a medical manipulator.

Description of Related Art

In the related art, a medical manipulator is known which is introduced into a patient's body for observation and treatment. The medical manipulator includes a bendable section in a distal end portion, and an orientation of the distal end portion can be changed inside the body.

As one of structures of the bendable section, a structure is known in which a plurality of cylindrical members (joint elements) such as joint rings and bending frames are arranged side by side in an axial direction.

According to the above-described structure, as the number of the joint elements to be arranged increases, it is possible to increase a maximum bending angle of the bending section. On the other hand, in a case where the bending section is bent at a certain bending angle, a radius of curvature of the bending section becomes larger as the number of the joint elements increases. A space inside the body is limited. Accordingly, in a case where the structure has many joint elements and the bending section is bent at an angle equal to or smaller than the maximum bending angle, there is a possibility that the distal end portion of the medical manipulator may not be located at an optimal position for a target tissue.

With regard to the above-described problem, Japanese Unexamined Patent Application, First Publication No. 2015-23951 discloses a structure in which the bending section having many joint elements arranged therein is divided into a plurality of regions which can perform a bending operation independently of each other. According to the structure, only a portion of the bending section can be bent and other sections can be linearly held. Therefore, even in a case where the bending section is bent at the angle equal to or smaller than the maximum bending angle, it is possible to suppress an increase in the radius of curvature of the bending section.

SUMMARY OF THE INVENTION

According to a first aspect of the present invention, there is provided a medical manipulator including an insertion portion comprising a bending portion including a plurality of joint elements, the bending portion being configured to be bendable; an end effector provided in a distal end portion of the insertion portion; a bend restraining unit configured to be movable relative to the insertion portion so as to restrain the joint elements; a position detector configured to detect a position of the bend restraining unit with respect to the insertion portion; an operation unit provided in a proximal end portion of the insertion portion; a first drive unit configured to generate a drive force for driving the bending portion; and a control unit configured to generate a first drive signal for driving the first drive unit based on an output from the operation unit and the position of the bend restraining unit.

According to a second aspect of the present invention, there is proved a manipulation method of a medical manipulator including a bending portion, and a bend restraining unit configured to restrain the bending portion. The method includes acquiring a restraint state of the bending portion from a sensor; acquiring an operation signal from an operation unit configured to operate the bending portion; generating a first drive signal for driving the bending portion based on the operation signal and the restraint state; and transmitting the first drive signal to a first actuator configured to generate a drive force for driving the bending portion.

According to a third aspect of the present invention, there is proved a medical manipulator including an insertion portion comprising a bending portion; an end effector provided in a distal end portion of the insertion portion; a bend restraining unit configured to restrain the bending portion; a sensor configured to detect a restraint state of the bending portion by the bend restraining unit; an operation unit provided in a proximal end portion of the insertion portion; a first actuator configured to generate a drive force for driving the bending portion; and a controller comprising one or more processors, the one or more processors configured to generate a first drive signal for driving the first drive unit based on an output from the operation unit and the restraint state of the bending portion.

BRIEF DESCRIPTION OF THE DRAWINGS

FIG. 6 is a view schematically showing an external configuration of a laparoscope according to a second embodiment of the present invention.

DETAILED DESCRIPTION OF THE INVENTION

Figure 1:
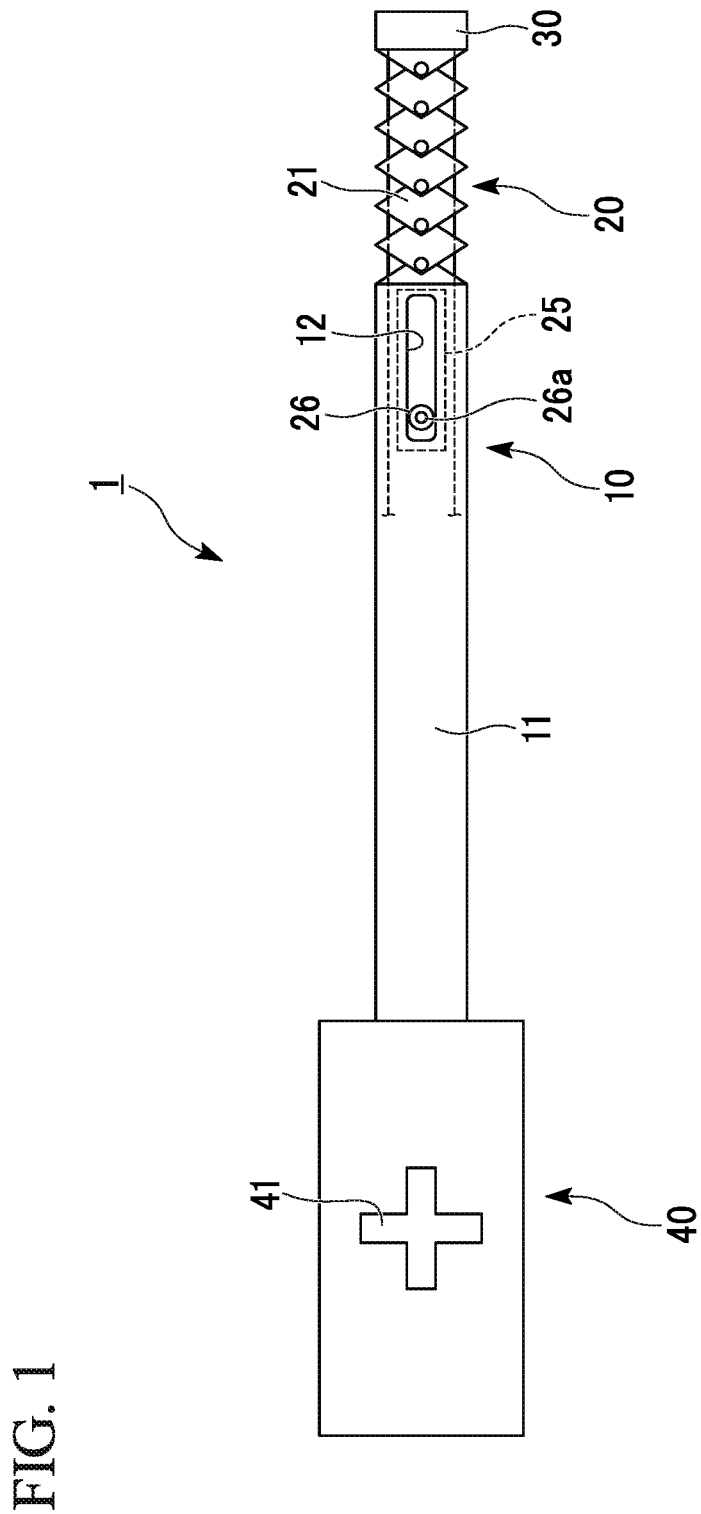
FIG. 1 is a view schematically showing an external configuration of a laparoscope according to a first embodiment of the present invention.
Figure 2:
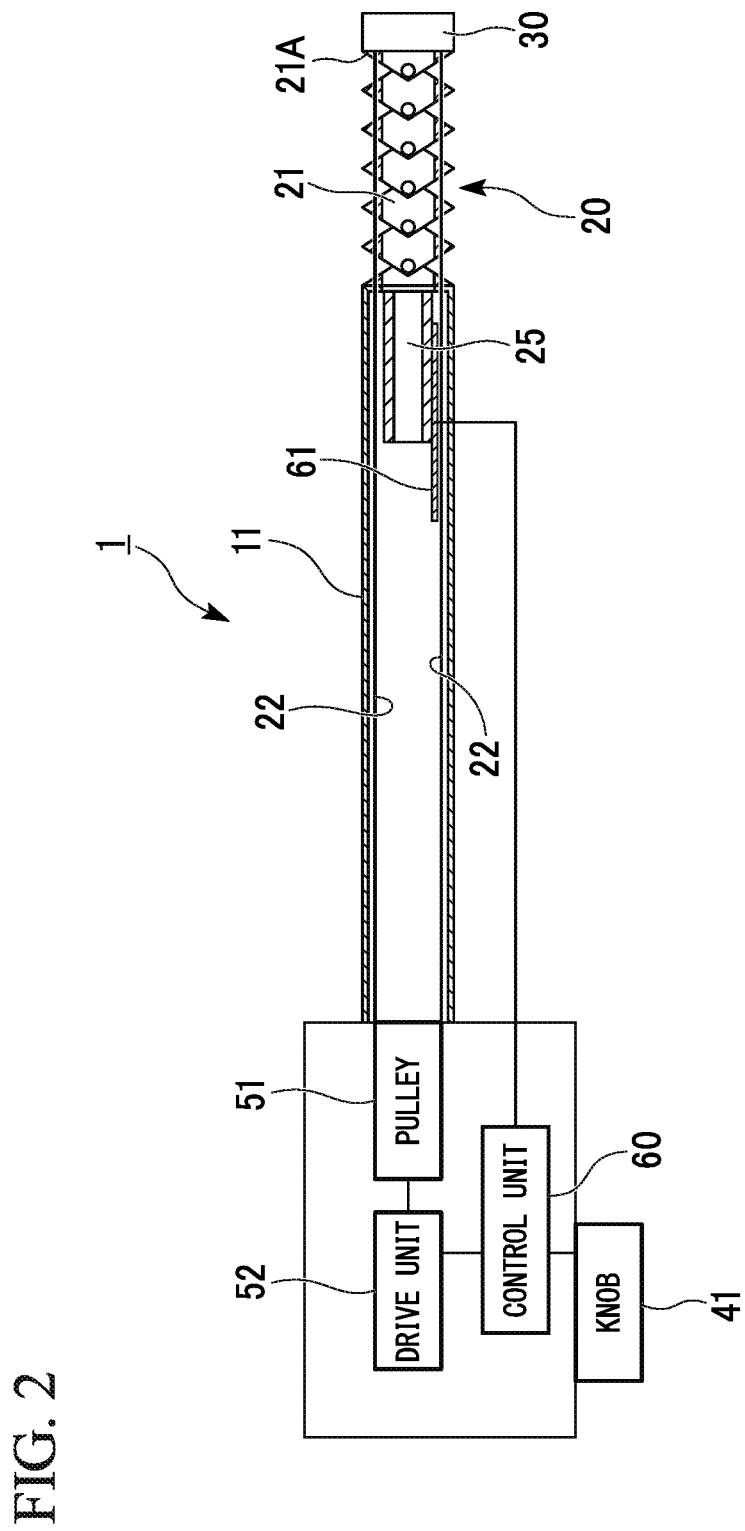
FIG. 2 is a view schematically showing a mechanism of the laparoscope.

A first embodiment according to the present invention will be described with reference to FIGS. 1 to 5B. FIG. 1 is a view schematically showing an external configuration of a laparoscope 1 which is a medical manipulator according to the present embodiment. FIG. 2 is a view schematically showing a mechanism of the laparoscope 1. As shown in FIG. 1, the laparoscope 1 includes an insertion portion 10 to be inserted into a patient's body, an imaging unit (end effector) 30 attached to a distal end portion of the insertion portion 10, and an operation unit 40 attached to a proximal end portion of the insertion portion 10.

The insertion portion 10 includes a rigid tubular portion 11 having no flexibility and a bending portion 20 provided on a distal end side of the tubular portion 11.

The tubular portion 11 is formed of metal. A wire (not shown) for supplying power to the imaging unit 30 and a cable (not shown) for transmitting or receiving information to or from the imaging unit 30 are inserted into the tubular portion 11. A slot 12 which communicates with a lumen and extends in a longitudinal direction is provided on an outer peripheral surface of the tubular portion 11.

The bending portion 20 has a plurality of joint elements 21 such as joint rings and bending frames. A basic structure thereof is known. As shown in FIG. 2, a drive member 22 such as a wire is inserted into the joint element 21. A distal end of the drive member 22 is fixed to a joint element 21A located on a most distal end side. An encoder (not shown) is attached to each of the joint elements 21. In this manner, a configuration is adopted to be capable of detecting a relative rotation amount of each joint element 21 with respect to the adjacent joint element.

A bend restraining unit 25 is located inside the tubular portion 11. The bend restraining unit 25 is a rigid tubular member, and is located so as to be capable of being advanced to and retracted from (movable forward to and rearward from) the tubular portion 11 in an axial direction. A protruding portion 26 is provided on outer peripheral surface of the bend restraining unit 25. The protruding portion 26 is positioned inside the slot 12 of the tubular portion 11. A round hole 26a that has a bottom portion is provided on an upper surface of the protruding portion 26 is provided with. A height of the protruding portion 26 is set to a value which does not allow the protruding portion to protrude from the slot 12.

The imaging unit 30 has an imaging element (not shown) or an illumination mechanism, and a basic structure thereof is well-known. As the imaging unit 30, it is possible to appropriately select and employ a structure of the imaging unit used for a known endoscope.

The operation unit 40 includes a knob 41 used by a user when designating a bending direction of the bending portion 20.

As shown in FIG. 2, a pulley 51, a drive unit (first drive unit) 52, and a control unit 60 are arranged inside the operation unit 40. A proximal end portion of the drive member 22 is connected to the pulley 51. For example, the drive unit 52 is configured to include a motor and is connected to the pulley 51 so as to be capable of transmitting a drive force.

The control unit 60 is electrically connected to the knob 41 and the drive unit 52, and generates a drive signal for driving the drive unit 52, based on an operation on the knob 41. The control unit 60 transmits the generated drive signal to the drive unit 52.

As shown in FIG. 2, a position detector (position sensor) 61 for detecting a relative position of the bend restraining unit 25 with respect to the tubular portion 11 is provided inside the tubular portion 11. A configuration of the position detector 61 is not particularly limited as long as the position of the bend restraining unit 25 can be detected with respect to the tubular portion 11. For example, the position detector 61 can be configured to employ a known linear encoder or a potentiometer.

The position detector 61 is connected to the control unit 60, and position information of the bend restraining unit 25 which is detected by the position detector 61 is transmitted to the control unit 60.

An operation when using the laparoscope 1 according to the present embodiment configured as described above will be described.

As preparatory work, a user opens a hole on a body wall such as an abdominal wall of a patient, and inserts a trocar into the hole so that the trocar indwells the body wall. If necessary, the user performs treatment on pneumoperitoneum, and establishes an environment where the laparoscope 1 can be inserted into the body of the patient.

Subsequently, the user assumes a usage mode of the laparoscope 1 and sets a maximum bending angle required when the bending portion 20 is used. Thereafter, the user adjusts a position of the bend restraining unit 25, based on the set maximum bending angle when the bending portion 20 is used. The position of the bend restraining unit 25 is adjusted by inserting a rod into the round hole 26a of the protruding portion 26 and by moving the protruding portion 26 inside the slot 12.

For example, when the maximum bending angle in view of the structure of the bending portion 20 is 180°, that is, when the imaging unit 30 substantially faces the proximal side, in a case where the maximum bending angle is set to 90°, the bend restraining unit 25 protrudes from the distal end of the tubular portion 11, and adjusts the position of the bend restraining unit 25 to such an extent that the distal end of the bend restraining unit 25 reaches a substantially intermediate portion of the bending portion 20.

After adjusting the position of the bend restraining unit 25, the user inserts the laparoscope 1 into the body of the patient and uses the laparoscope 1. In a case where the user wants to change an orientation of the imaging unit 30 when using the imaging unit 30, the user operates the knob 41 of the operation unit 40 so as to designate a bending direction and a bending amount (bending angle) of the bending portion 20.

The control unit 60 receiving an output (operation signal) from the knob 41 acquires the position information of the bend restraining unit 25 from the position detector 61 (position information acquisition step). Based on the position information acquired from the position detector 61, the control unit 60 identifies the number of the joint elements restrained by the bend restraining unit 25 so not to be rotated out of the joint elements 21 of the bending portion 20, thereby identifying a restraint state of the bending portion 20 restrained by the bend restraining unit 25 (restraint state identification step).

The control unit 60 may be configured to receive the position of the bend restraining unit 25 when the output is received (acquired) from the knob 41, or may be configured to receive the position of the bend restraining unit 25 at a predetermined interval, irrespective of whether or not the control unit 60 receives the output from the knob 41.

Subsequently, the control unit 60 generates a drive signal (first drive signal) for driving the drive unit 52, based on the output from the knob 41 and the restraint state of the bending portion 20 and transmits the drive signal to the drive unit 52 (drive signal generation step). For example, as in the above-described example, in a case where the maximum bending angle is set to 90° when the bending portion 20 is used, even if the output from the knob 41 indicates the bending angle of 120°, the control unit 60 generates the drive signal after correcting the bending angle to 90° of the maximum bending angle when the bending portion 20 is used.

The drive unit 52 is driven based on the drive signal received from the control unit 60. As a result, the pulley 51 is rotated, and the drive member 22 is pushed and pulled, thereby driving the bending portion 20 so as to be bent in a desired direction. In this case, the joint elements 21 into which the bend restraining unit 25 is inserted are restrained so as not to be rotated even if the drive member 22 is pushed and pulled, thereby maintaining a linear state where the joint elements are arranged side by side along an axis of the tubular portion 11. Therefore, in the bending portion 20, only the joint elements 21 which are not restrained by the bend restraining unit 25 are rotated so as to be bent at a predetermined bending angle.

Figure 3A:
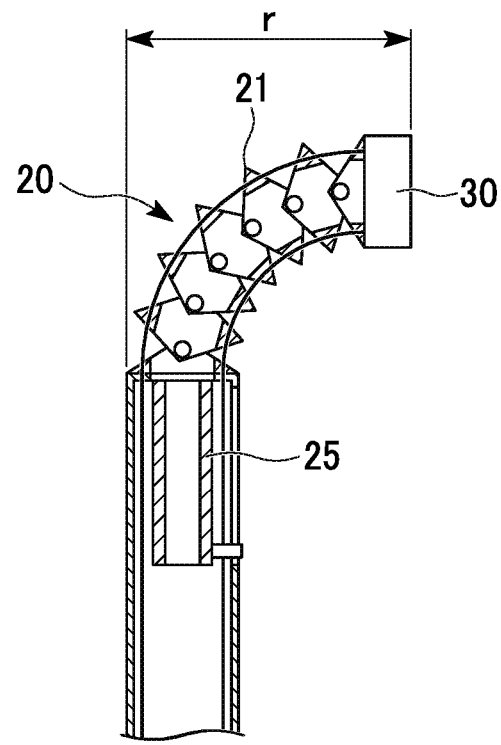
FIG. 3A is a view showing an example in which the laparoscope is bent in a state where joint elements are not restrained.
Figure 3B:
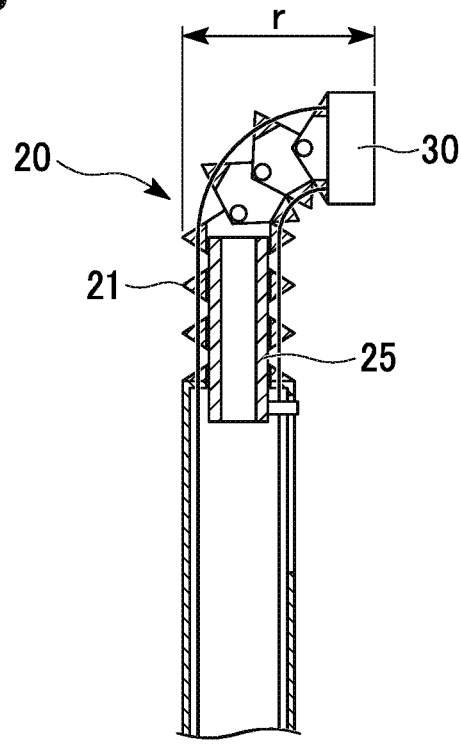
FIG. 3B is a view showing an example in which the laparoscope is bent in a state where some of the joint elements are restrained.

FIG. 3A shows an example in which the orientation of the imaging unit 30 is bent at 90° in a state where the bend restraining unit 25 does not restrain the joint elements 21 at all. FIG. 3B shows an example in which the orientation of the imaging unit 30 is bent at 90° in a state where the bend restraining unit 25 restrains some of the joint elements 21. Although the bending angles of the imaging unit 30 are the same as each other, it is understood that a radius of curvature r of the bending portion 20 is smaller in FIG. 3B.

As described above, according to the laparoscope 1 of the present embodiment, some of the joint elements 21 of the bending portion 20 can be restrained by moving the bend restraining unit 25 relative to the tubular portion 11. Therefore, the joint elements 21 can be restrained using a simple structure so as to reduce the radius of curvature of the bending portion 20. As a result, it is possible to preferably and compatibly to increase the maximum bending angle in a state where the joint elements are not restrained and to reduce the radius of curvature when the bending angle is small.

In addition, the control unit 60 automatically generates a proper drive signal, based on the output from the knob 41 and the restraint state of the bending portion 20 restrained by the bend restraining unit 25. Accordingly, in view of the restraint state, the bending portion 20 can be preferably operated. As a result, it is possible to preferably prevent breakage of the bending portion 20 or a sudden shape change therein.

Furthermore, the protruding portion 26 used in adjusting the position of the bend restraining unit 25 is configured not to protrude from the slot 12 onto the outer peripheral surface of the tubular portion 11. Accordingly, the protruding portion 26 does not hinder an operation of the laparoscope 1 inserted into or removed from a patient.

In the present embodiment, a process performed by the control unit 60 in order to generate the proper drive signal is not limited to a change in the bending angle value. For example, speed for pushing and pulling the drive member 22 may be changed depending on the restraint state. In a case where the bending angles are the same as each other, the rotation amount per one joint element increases as the number of the restrained joint elements increases. Therefore, the speed for pushing and pulling the drive member 22 may be increased as the number of the restrained joint elements increases. In this manner, the speed may be controlled so that a time required for bending the joint elements 21 at a predetermined angle is substantially constant. Alternatively, the speed for pushing and pulling the drive member 22 may be decreased as the number of the restrained joint elements increases. In this manner, the speed may be controlled so as to suppress a sudden shape change in the bending portion 20.

In addition, various forms are conceivable for the configuration and arrangement of the bend restraining unit.

Figure 4A:
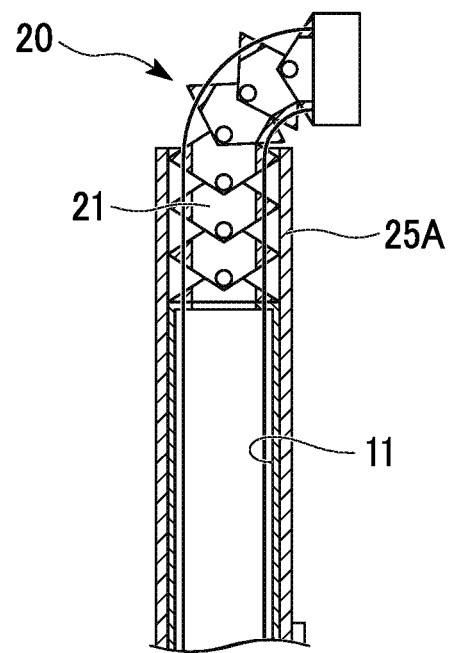
FIG. 4A is a schematic view showing another example of a bend restraining unit.

A bend restraining unit 25A shown in FIG. 4A is located outside the tubular portion 11 by the inserting the tubular portion 11 into the bend restraining unit 25A. If the bend restraining unit 25A moves forward to the tubular portion 11, a portion of the bending portion 20 entering the inside of the bend restraining unit 25A, thereby restraining the joint elements 21.

Figure 4B:
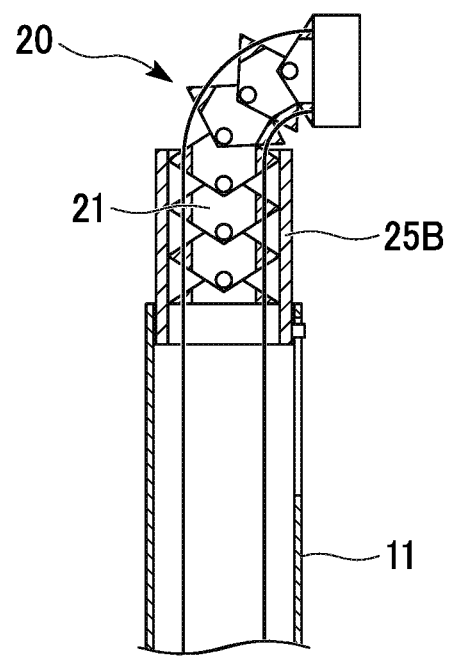
FIG. 4B is a schematic view showing another example of the bend restraining unit.

Similar to the bend restraining unit 25A, a bend restraining unit 25B shown in FIG. 4B restrains the joint elements 21 by covering a portion of the bending portion 20. However, similar to the bend restraining unit 25 according to the first embodiment, the bend restraining unit 25B is located inside the tubular portion 11.

Figure 5A:
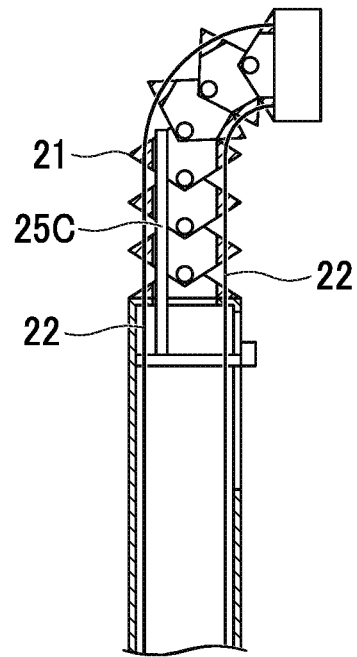
FIG. 5A is a schematic view showing another example of the bend restraining unit.

A bend restraining unit 25C shown in FIG. 5A is a rod inserted into a hole (not shown) in the joint elements 21. The hole into which the bend restraining unit 25C is inserted is provided in a phase different from that of the hole into which the drive member 22 is inserted in a circumferential direction of the joint element 21. Accordingly, the hole does not interfere with the movement of the drive member 22. The rod used as the bend restraining unit 25C may have either a hollow tubular shape or a solid stick shape.

Figure 5B:
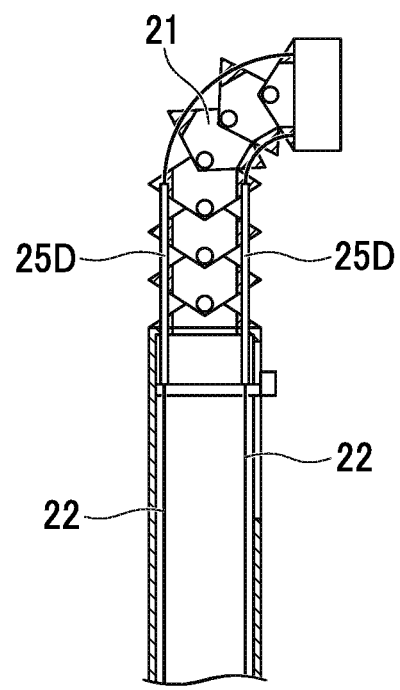
FIG. 5B is a schematic view showing another example of the bend restraining unit.

A bend restraining unit 25D shown in FIG. 5B is a pipe into which the drive member 22 is inserted. The bend restraining unit 25D is inserted into a hole which is provided in the joint elements 21 and into which the drive member 22 is inserted so as to be movable forward to or rearward from the hole.

In view of the rigidity required for restraint (rigidity to such an extent that the linear state can be maintained even when the drive member 22 is pushed and pulled), one or more bend restraining units 25C or bend restraining unit 25D may be appropriately located.

In a case where the bend restraining unit 25C or the bend restraining unit 25D is inserted into the hole provided in the joint elements, the internal space of the insertion portion is not reduced. Accordingly, it is advantageous in that a large space is available in order to incorporate a component such as a cable connected to the imaging unit.

Next, a second embodiment according to the present invention will be described with reference to FIGS. 6 to 9. A laparoscope 101 according to the present embodiment is different from the above-described laparoscope 1 in that the position of the bend restraining unit is adjusted using an operation unit disposed on an operator's hand side. In the following description, the same reference numerals will be given to the repeatedly described configurations, and a description thereof will be omitted.

FIG. 6 is a view schematically showing an external configuration of the laparoscope 101. In addition to the knob 41, the operation unit 40 has a slide bar (position adjuster) 142 used in adjusting the position of the bend restraining unit 25.

Figure 7:
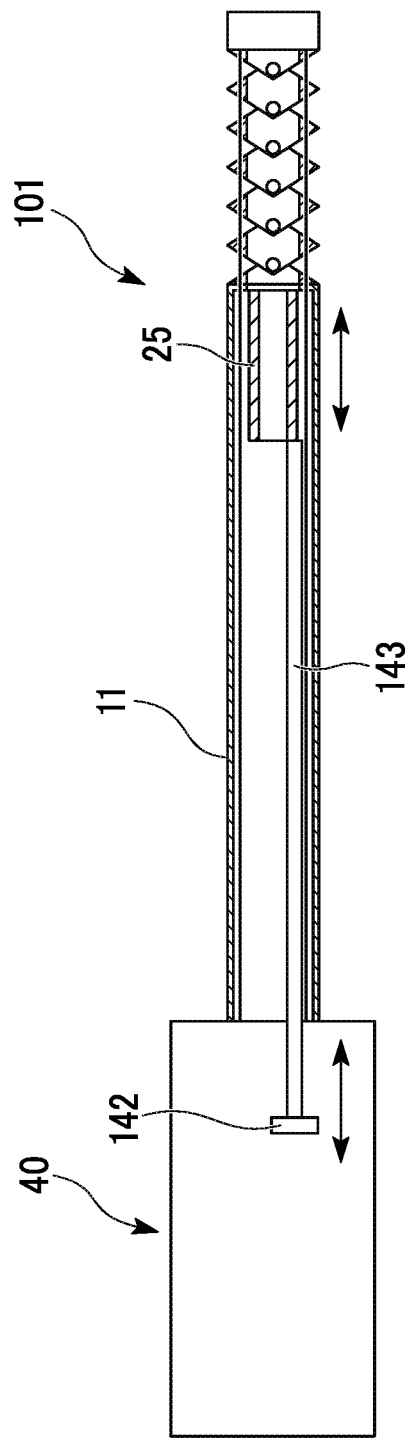
FIG. 7 is a view schematically showing a drive mechanism of a bend restraining unit in the laparoscope.

FIG. 7 is a schematic view showing a mechanism for driving the bend restraining unit in the laparoscope 101. Other mechanisms are omitted in the illustration. The bend restraining unit 25 and a slide bar 142 are connected to each other using a shaft 143 inserted into the tubular portion 11. Therefore, the bend restraining unit 25 moves forward to or rearward from the tubular portion 11 in conjunction with the movement of the slide bar 142.

According to the laparoscope 101 of the present embodiment, similar to the laparoscope 1 of the first embodiment, it is also possible to preferably and compatibly to increase the maximum bending angle in a state where the joint elements are not restrained and to reduce the radius of curvature when the bending angle is small.

In addition, the position of the bend restraining unit 25 can be adjusted by operating the slide bar 142 disposed in the operation unit 40. Accordingly, even in a state where the laparoscope 101 is inserted into a patient's body, the position of the bend restraining unit 25 can be adjusted. As a result, the bending portion can always be operated using the optimal radius of curvature by changing the position of the bend restraining unit during a medical procedure.

In the present embodiment, the structure which enables the position of the bend restraining unit to be adjusted in the operation unit is not limited to an example of using the above-described shaft.

Figure 8:
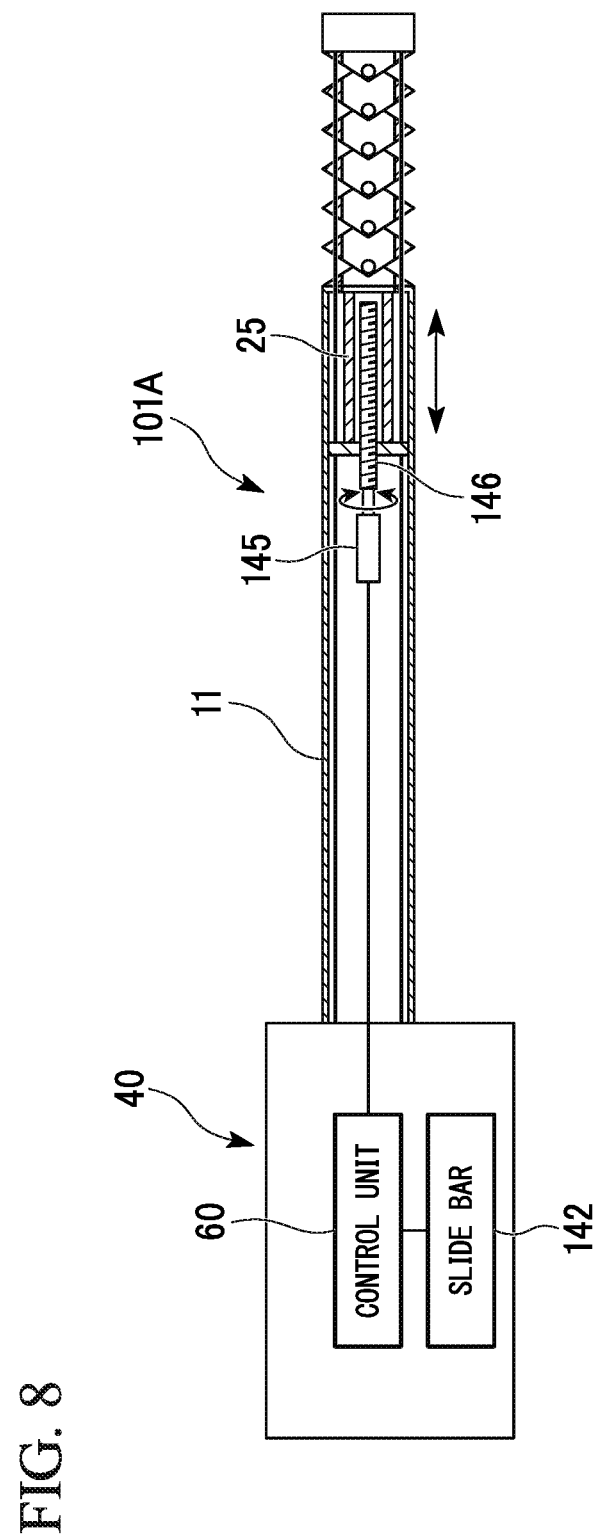
FIG. 8 is a view schematically showing a drive mechanism of a bend restraining unit according to a modification example of the laparoscope.

In a laparoscope 101A according to a modification example shown in FIG. 8, the bend restraining unit 25 is driven by a motor (second drive unit) 145. The slide bar 142 is connected to the control unit 60. The control unit 60 generates a drive signal for driving the motor 145, based on an operation output from the slide bar 142, and transmits the drive signal to the motor 145.

A ball screw 146 is connected to the motor 145. If the motor 145 is driven, the ball screw 146 is rotated, and the bend restraining unit 25 moves forward to or rearward from the tubular portion 11.

In the laparoscope 101A, the motor 145 may be located inside the operation unit 40 by extending the ball screw 146 or a shaft member connected to the ball screw 146 to the operation unit 40. In this case, the second drive unit can prevent a decrease in the internal space of the insertion portion.

Furthermore, in a case where the bend restraining unit is electrically driven as in the laparoscope 101A, the bend restraining unit 25 may be automatically driven by the control unit 60 in accordance with a user's operation performed on the bending portion 20. Hereinafter, an example of the automatic drive will be described.

Figure 9:
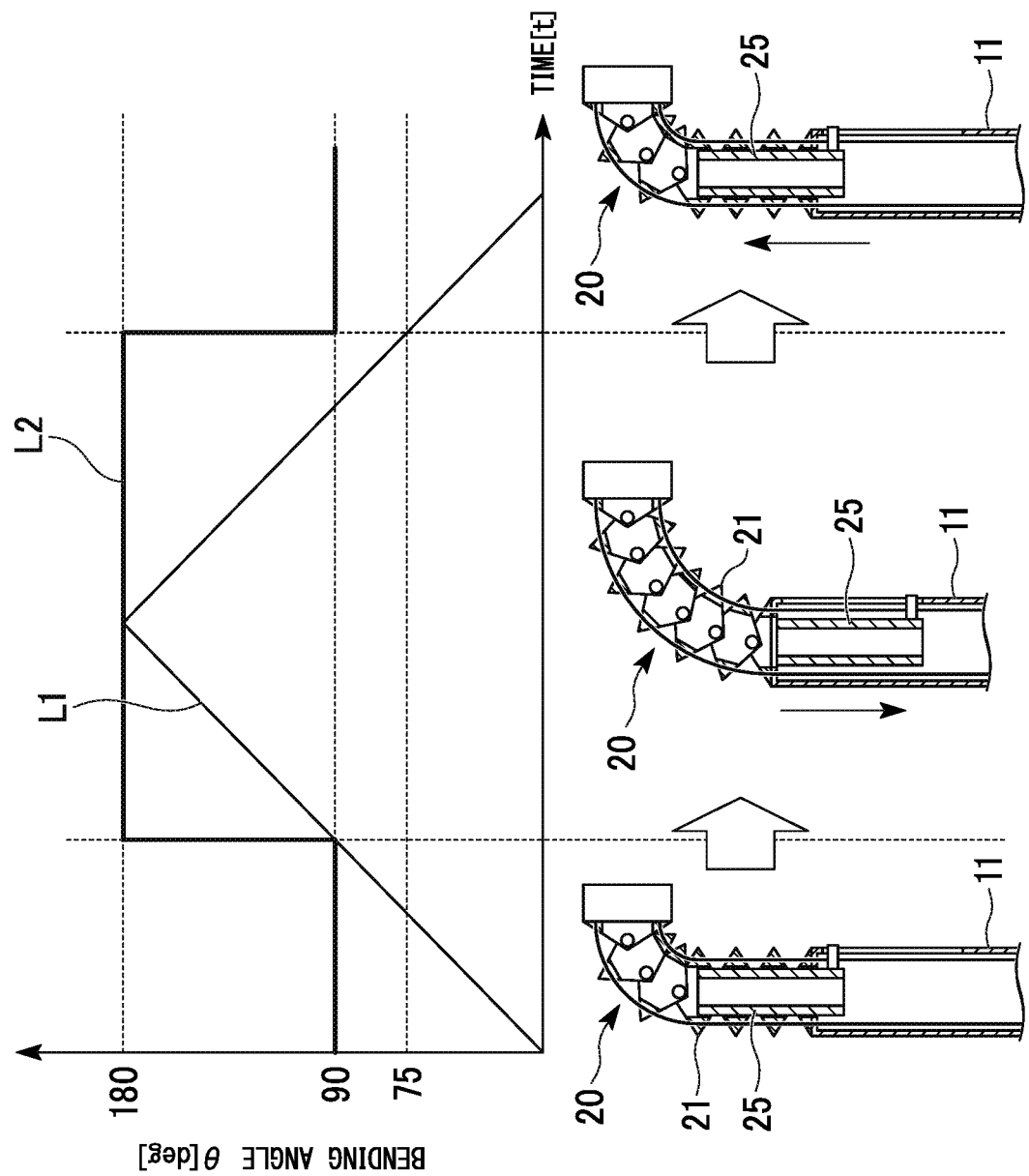
FIG. 9 is a graph showing an example of an automatic drive mode of the bend restraining unit controlled by a control unit.

FIG. 9 is a graph showing an example of an automatic drive mode of the bend restraining unit 25 controlled by the control unit 60. In FIG. 9, a vertical axis indicates a bending angle $\theta$ of the bending portion 20, and a horizontal axis indicates a time t. In this example, the bend restraining unit 25 restrains some of the joint elements 21 in an initial state, and the maximum bending angle is set to 90° when the bending portion is used.

A command value of the bending angle for the bending portion 20 output from the knob 41 by a user's operation gradually increases as indicated by a line L1. If the command value exceeds 90° (first threshold value) which is the maximum bending angle when in use, the control unit 60 generates a drive signal (second drive signal) for driving the bend restraining unit 25 and causes the bend restraining unit 25 to move rearward, thereby releasing the restrained joint elements 21. As a result, the maximum bending angle is updated from 90° to 180° as indicated by a line L2 when the bending portion 20 is used. In this manner, the bending portion 20 can be bent to have an angle corresponding to the command value.

Thereafter, if the command value of the bending angle decreases and becomes equal to or smaller than 75° (second threshold value) which can correspond to the bend restraining unit 25 in the initial state, the control unit 60 generates the second drive signal and causes the bend restraining unit 25 to move forward, thereby moving the bend restraining unit 25 to a position in the initial state. As a result, the bending portion 20 can be bent to have an angle corresponding to the command value with the smaller radius of curvature.

According to this a modification example, the control unit 60 automatically drives the bend restraining unit 25, based on the user's operation performed on the bending portion 20 and the position of the bend restraining unit 25. Accordingly, the user does not need to adjust the bend restraining unit during the medical procedure, and a simple operation enables the user to minimize the radius of curvature of the bending portion.

In this modification example, an example has been described in which the bend restraining unit is automatically driven so that the maximum bending angle is either 90° or 180° when in use. However, the threshold value for the automatic drive may be set so that the maximum bending angle is changed in three or more stages.

In this modification example, an example has been described in which the first threshold value serving as the threshold value for the automatic drive when the command value increases is different from the second threshold value serving as the threshold value for the automatic drive when the command value decreases. However, the first threshold value and the second threshold value may be the same as each other. However, as in the above-described example, since the second threshold value is smaller than the first threshold value, there is an advantage as follows. It is possible to prevent the bend restraining unit from being frequently operated in a case where the command value is minutely changed around the first threshold value.

Hitherto, the embodiments according to the present invention have been described. However, the technical scope of the present invention is not limited to the above-described embodiments. The combination of the configuration elements can be changed within the scope not departing from the gist of the present invention. The respective configuration elements can additionally have various modifications or can be deleted.

Figure 10:
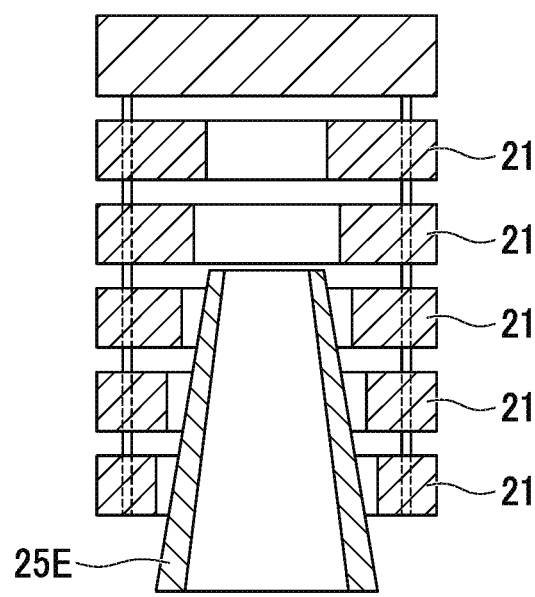
FIG. 10 is a schematic view showing a bend restraining unit and joint elements according to a modification example of the present invention.

For example, as in a modification example shown in FIG. 10, a bend restraining unit 25E may be used which has a shape narrowed as the shape is closer to the distal end and whose cross-sectional area gradually decreases. In this manner, the plurality of joint elements 21 may be configured so that the cross-sectional area of the internal space of the bending portion gradually decreases as the internal space is closer to the distal end of the insertion portion 10. According to this configuration, even in a state where the bending portion is bent, the bend restraining unit is caused to move forward so as to allow the distal end portion of the bend restraining unit to easily enter the internal space of the bending portion. Therefore, the position of the bend restraining unit is easily adjusted during the medical procedure. In this modification example, a shape of the joint elements and a cross-sectional shape of the internal space are not particularly limited.

In the above-described respective embodiments, an example has been described in which the laparoscope including the imaging unit is used as the end effector. However, the end effector of the medical manipulator according to the present invention is not limited to the imaging unit. Therefore, the configuration according to the present invention may be applied to the medical manipulator which includes a treatment unit appropriately selected from various treatment units known as the end effector and which is used for performing a predetermined treatment.

Furthermore, in the above-described respective embodiments, an example has been described in which the so-called rigid medical manipulator employs the insertion portion including the rigid tubular portion. However, the present invention is also applicable to the flexible medical manipulator whose insertion portion is flexible.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical manipulator comprising:
   an insertion portion comprising a bending portion including a plurality of joint elements, the bending portion being configured to be bendable;
   an end effector provided in a distal end portion of the insertion portion;
   a bend restraining unit configured to be movable relative to the insertion portion so as to restrain the joint elements;
   a position detector configured to detect a position of the bend restraining unit with respect to the insertion portion;
   an operation unit provided in a proximal end portion of the insertion portion;
   a first drive unit configured to generate a drive force for driving the bending portion; and
   a control unit configured to generate a first drive signal for driving the first drive unit based on an output from the operation unit and the position of the bend restraining unit.

2. The medical manipulator according to claim 1,
   wherein the operation unit comprises a position adjuster for moving the bend restraining unit relative to the insertion portion.

3. The medical manipulator according to claim 1, further comprising:
   a second drive unit configured to generate the drive force for driving the bend restraining unit,
   wherein the control unit is configured to generate a second drive signal for driving the second drive unit based on the output from the operation unit and the position of the bend restraining unit.

4. The medical manipulator according to claim 1,
   wherein the bending portion is configured so that a cross-sectional area of an internal space gradually decreases as the internal space is closer to a distal end, and
   wherein the bend restraining unit is configured so that a cross-sectional area of the bend restraining unit gradually decreases as the bend restraining unit is closer to the distal end, and the bend restraining unit is configured to enter into the internal space of the bending portion.

5. A manipulation method of a medical manipulator including a bending portion, and a bend restraining unit configured to restrain the bending portion, the method comprising:

acquiring a restraint state of the bending portion from a sensor;
   acquiring an operation signal from an operation unit configured to operate the bending portion;
   generating a first drive signal for driving the bending portion based on the operation signal and the restraint state; and
   transmitting the first drive signal to a first actuator configured to generate a drive force for driving the bending portion.

6. The manipulation method of a medical manipulator according to claim 5, further comprising:
   generating a second drive signal for driving the bend restraining unit based on the operation signal and the restraint state, and
   transmitting the second drive signal to a second drive unit that generates a drive force for driving the bending restraining unit.

7. The manipulation method of a medical manipulator according to claim 5,
   wherein the bend restraining unit configured to restrain the bending portion by moving relative to the insertion portion.

8. The manipulation method of a medical manipulator according to claim 7,
   wherein the sensor is a position sensor that is configured to detect a position of the bend restraining unit with respect to the insertion portion.

9. A medical manipulator comprising:
   an insertion portion comprising a bending portion;
   an end effector provided in a distal end portion of the insertion portion;
   a bend restraining unit configured to restrain the bending portion;
   a sensor configured to detect a restraint state of the bending portion by the bend restraining unit;
   an operation unit provided in a proximal end portion of the insertion portion;
   a first actuator configured to generate a drive force for driving the bending portion; and
   a controller comprising one or more processors, the one or more processors configured to generate a first drive signal for driving the first drive unit based on an output from the operation unit and the restraint state of the bending portion.

10. The medical manipulator according to claim 9, further comprising:
    a second actuator configured to generate the drive force for driving the bend restraining unit,
    wherein the one or more processors configured to generate second drive signal for driving the second drive unit based on the output and the restraint state of the bending portion.

11. The medical manipulator according to claim 9,
    wherein the bend restraining unit is configured to move relative to the insertion portion.

12. The medical manipulator according to claim 11,
    wherein the bending portion is configured so that a cross-sectional area of an internal space gradually decreases as the internal space is closer to a distal end, and
    wherein the bend restraining unit is configured so that a cross-sectional area of the bend restraining unit gradually decreases as the bend restraining unit is closer to the distal end, and the bend restraining unit is configured to enter into the internal space of the bending portion.

13. The medical manipulator according to claim 11, wherein the sensor is a position sensor configured to detect a position of the bend restraining unit with respect to the insertion portion.
14. The medical manipulator according to claim 9, wherein the operation unit has a position adjuster configured to adjust a position of the bend restraining unit by moving the bend restraining unit relative to the insertion portion.

* * * * *